(12) United States Patent
Kuderer (10) Patent No.: US 7,117,109 B2
(45) Date of Patent: Oct. 3, 2006

(54) PROCEDURE FOR PROCESSING MEASURING DATA AND DEVICE TO PERFORM THE PROCESS

(75) Inventor: Hubert Kuderer, Waldbronn (DE)

(73) Assignee: Agilent Technologies, Inc., Palo Alto, CA (US)

( * ) Notice: Subject to any disclaimer, the term of this patent is extended or adjusted under 35 U.S.C. 154(b) by 824 days.

(21) Appl. No.: 10/180,611

(22) Filed: Jun. 26, 2002

(65) Prior Publication Data

US 2003/0158716 A1    Aug. 21, 2003

(30) Foreign Application Priority Data

Jan. 30, 2002    (EP)    .................. 02002215

(51) Int. Cl.
*G01D 18/00*    (2006.01)
*G06F 19/00*    (2006.01)

(52) U.S. Cl. .................. 702/86; 700/54; 702/105; 703/6

(58) Field of Classification Search .................. 702/85, 702/86, 95, 105, 183, 185; 700/37, 52, 54; 703/2, 6
See application file for complete search history.

(56) References Cited

U.S. PATENT DOCUMENTS

| | | | | |
|---|---|---|---|---|
| 5,592,402 A | * | 1/1997 | Beebe et al. | .................. 703/6 |
| 6,850,806 B1 | * | 2/2005 | Yutkowitz | .................. 700/54 |
| 6,859,747 B1 | * | 2/2005 | Yutkowitz | .................. 702/105 |

FOREIGN PATENT DOCUMENTS

| | | |
|---|---|---|
| EP | 0 222 612 | 5/1987 |
| EP | 0 294 121 | 12/1988 |
| EP | 0 295 966 | 12/1988 |
| EP | 0 299 652 | 1/1989 |
| WO | WO 93/21592 | 10/1993 |

* cited by examiner

*Primary Examiner*—Bryan Bui
*Assistant Examiner*—John Le (57) ABSTRACT

A method for processing measuring data and a device to perform the method, wherein the measuring data can be determined by using a measurement system, more particularly a chromatographic analyzing system, for the measurement of measuring values that correspond to certain information about, or of, a technical process and that depend on at least two variables.

19 Claims, 2 Drawing Sheets

PROCEDURE FOR PROCESSING MEASURING DATA AND DEVICE TO PERFORM THE PROCESS

FIELD OF THE INVENTION

The invention concerns a procedure for processing measuring data that can be measured by using a measurement system for measuring data, which corresponds to certain useful information about, or of, a technical process, and which depend on at least two variables, and a device to carry out the procedure.

DISCUSSION OF THE BACKGROUND ART

Such a two-dimensional measuring data structure can be found, for example, in analytic measurement systems, in particular in the field of UV/VIS absorption measurement technology. In this case, diode array detectors (DAD's) are used. Diode array detectors are constantly gaining importance because, firstly, the UV/VIS absorption measurement procedure represents the most significant of the various analytic detection techniques and, secondly, DAD's generate online signals corresponding to the wavelength (spectra) and to time (chromatograms). UV/VIS absorption measurement technology is a good compromise between high sensitivity, high selectivity, and linear measuring range over several orders of magnitude. From the two-dimensional data structure, information about the identity (spectra) of the substances to be analyzed and about the amount of the sample substance (concentration) may be derived.

In traditional procedures, the concentration course of the substance to be studied is measured along the time axis for selected wavelengths after the substances of a sample mixture have been separated with respect to time, using a chromatographic analyzing technique. The measurement wavelength in this case is selected for optimum measuring conditions according to the absorbance of the respective substance. This means that, at lower concentrations, a wavelength with high extinction is used while a wavelength with low extinction is rather used for high concentrations. A wavelength with medium extinction may be used as a compromise. The respective substance amount may be determined from the concentration course by integration over time with appropriate gauging.

The spectra are determined from the data points along the wavelength axis. The spectra exhibit a substance-specific spectral characteristic that is used to identify the measured substance. The identification is done by comparison with spectra of known substances. Often information on the completeness of the separation is also derived from the measuring data measured. This is done by comparing the spectrum at the start of a chromatographic peak to the spectrum of the peak maximum or the spectrum at the end of a peak. If the spectra only differ by a factor, it is assumed that the peak at hand was completely separated during the analysis. The substance amount of the corresponding peak can then be determined correctly.

For measurement systems using DAD's, the measured data is subject to a number of undesired influence quantities that can affect the accuracy and reliability of the measuring results. Such influence quantities are either due to the shortcoming of the system components used and to the variations of environmental conditions or due to the selection of the analysis parameters according to the measurement method.

Such influence quantities include the intensity stability and the spatial expansion of the plasma of the light source, alterations of the optical projection due to thermal expansion of the system, changes to the optical ray trajectory due to the solvent or flow-related processes in the flux cell (index of refraction, flow profile, etc.), influencing of the measurement system due to disturbances by other modules (e.g. pressure surges, pump ripples, etc.), disturbances affecting the measurement system from the outside and altering the signals, degradation or alteration effects of system components used, thermal heating or transient behavior, random noise or pattern noise, and similar disturbances.

Regarding the Stability of the Light Source:

Spectrophotometric measurement systems often use gas-discharge lamps (e.g. deuterium lamps) as light sources. After the ignition process, a radiant plasma is created between the anode and the cathode of such a light source. The intensity and the spatial expansion of the plasma are subject to variations in time, which are due to the stability of the power supply and the burning properties due to the technical layout of the individual lamp. Such variations in time cause errors in the measuring data.

Regarding the Thermal Expansion of the Optical Equipment:

Due to fluctuations of the environmental conditions and because of the thermal expansion of the materials used, the imaging properties of the optical equipment are affected. This also causes errors in the measuring results.

Regarding the Disturbance of the Optical Ray Trajectory Due to the Solvent and Flow-Related Processes in the Flux Cell:

During the analysis, the substances to be measured, which were separated in the column through chromatographic separation and dissolved in the mobile phase, are led through the flux cell. During the absorption measurement, the changes in intensity and in the spectral composition of the light due to the processes in the flux cell are measured. From this, the absorption course and, based on the Lambert-Beer law, the concentration course of the substances to be studied is determined. Using appropriate procedures, the substance amount of the sample to be studied can be calculated from these values.

Depending on the analysis method, the composition of the mobile phase is often purposely changed during the analysis in order to optimize the separation of the substances. This means that during the analysis, the optical properties of the mobile phase are also changing due to the dynamic change in index of refraction and absorption characteristics, thus sometimes considerably affecting the measuring results. The value for the static index of refraction of the mobile phase is also affected by temperature fluctuations. An addition, pressure fluctuations, caused by the solvent pumps, adversely affect the optical properties.

Regarding the Disturbance of the Results by Random Noise or Pattern Noise:

Random noise superimposed over the measuring values is caused by stochastic processes occurring during the emission of light by gas discharge and during the detection of the photons by a photo sensor. In addition, there are noise terms caused by the circuits of the electronic signal processing system or by influences of the surroundings. The characteristics of such noise terms can be subject to a statistical distribution function or be characterized by system-specific patterns.

The noise adversely affects the accuracy of the measuring results and reduces the limit of detectability of the measurement system. Up to now, this has been met with filtering the measuring data in the time and wavelength dimensions. However, this is done at the expense of the time or spectral resolution of the signals.

It has always been a challenge in the design of measurement devices to minimize the effects of influence quantities in order to avoid significantly distorting the measuring results. In the past, some complex approaches have been realized to fulfill the requirements. Corresponding to the complexity of the approaches, different results have been achieved.

In order to fulfill the highest possible demands with respect to accuracy and precision of the measuring results, so-called two-beam systems have been designed in the past in order to suppress the effects of the intensity instability and the spatial expansion of the light source. The optical light beams are split into a reference path and an analysis path. Assuming that the optical imaging properties are identical for both paths, disturbances may be eliminated by a calculation of ratio. On closer examination, however, it becomes evident that two optical paths with identical properties can hardly be realized. Difficulties occur because the analysis path contains the actual flux cell while a model of such a flux cell is contained in the reference path.

Changes in the optical properties due to disturbances inside the flux cell (index of refraction, solvent absorption, streaks, etc.) or due to the flux cell itself can therefore not be detected by reference creation.

When using traditional approaches, the problems resulting from the dependence of the index of refraction on different factors can only be improved through complicated optical constructions and usually only at the expense of the light flux rate. This adversely affects the limits of detectability.

Furthermore, it should be noted that because of the lower light flux rate due to the splitting of the optical ray trajectory on one hand and due to the additional noise source due to the reference path on the other hand, the noise contribution of the measurement system is made considerably worse. Not only are the costs increased compared to simpler designed measurement systems, but a number of unfavorable compromises have to be accepted as well.

In the meantime, technology has reached a state wherein hardly any improvements can be achieved through constructional measures with acceptable cost and effort.

Past endeavors to improve the accuracy and limit of detectability with the help of suitable algorithms were concentrated on filter algorithms that reduce the statistical uncertainty, i.e. the noise. However, the disadvantage of filtering the data is the adverse effect on the time and/or spectral resolution of the signals. Further efforts also become meaningless when the systematic error contributions are dominating and reducing the accuracy.

SUMMARY OF THE INVENTION

It is thus a task of the invention to create a procedure with which it is possible to achieve more accurate and more precise measuring results in a simple manner and/or to monitor the quality of the measurement system when using a measurement system to determine measuring values that depend on at least two variables.

This task is solved by the following measures:

a) Performing a calibration step, including:
   $a_1$) Stimulation of the measuring system by changing cause variables responsible for systematic measuring errors and determining the corresponding measuring data, using the measuring system;
   $a_2$) Determination of effect vectors corresponding to systematic measuring errors from the measuring data obtained in step $a_1$) by using a mathematical procedure, more particularly a factor analysis, wherein the effect vectors that correspond to the measuring errors are based on a mathematical model with which the measuring data can be estimated at least in approximation, except for a definable error (residue), and wherein the model contains at least one error term containing an effect vector assigned to an measuring error and a corresponding error contribution;

b) Performing a measuring step, including:
   $b_1$) Determining measuring data with the measurement system corresponding to certain useful information about, or of, the technical process while the technical process is taking place;
   $b_2$) Reducing the measuring data gathered in step $b_1$) to linear components, based on the effect vectors determined in step $a_2$) that correspond to the measuring errors, by using a mathematical procedure, more particularly a linear regression procedure, in order to determine the error contributions with which useful information, which are corrected for systematical measuring errors, can be determined.

The aim of the procedure according to the invention is to determine the effect vectors corresponding to the systematic measuring errors in a first calibration step. The effect vectors can be used to describe the properties of the shortcomings of the individual measurement system. In this step, the measurement system is stimulated by varying influence quantities causing systematic measuring errors. From the recorded data, the abstract effect vectors are then determined with mathematical methods. Since no carriers of useful information, e.g. certain substances, take part in the calibration cycle, the occurring variations of the measuring data are exclusively caused by undesired effects as a reaction to the stimulation. This means that the determined effect vectors exclusively correspond to systematic error terms.

In a following measuring step, for example in analytic measurements, the individual carriers of useful information, in particular the substances or substance mixtures to be analyzed, which were separated by chromatographic separation methods, are analyzed individually. At any point in time, the measuring data are separated into linear components using mathematical methods based on the effect vectors used. When doing so, the error contributions, i.e. the intensities of the respective error effects, are preferably determined with multi-linear regression or vector multiplication. Using these error contributions or error coefficients, the useful information corrected for the systematic measuring errors can be easily determined.

The procedure according to the invention is thus a particularly easy way of achieving measuring results that are much more accurate and precise than in the past. By separating the measured signal into all contributing effects in a suitable manner, this procedure can be used effectively for a signal analysis. This procedure can also be used effectively in the diagnosis of all kinds of disturbance effects, i.e. as a diagnostic aid for monitoring the measurement system.

Particularly advantageous areas of application for the procedure according to the invention are, apart from UV/VIS absorption measurement technology by using diode array detectors, diode array spectral photometers, fluorescence detectors based on lattices, nuclear spin technology, and ultrasonic technology.

The useful information is effectively determined from the measuring data, corrected for error contributions, by applying the mathematical algorithms on which the mathematical model is based.

According to an advantageous embodiment of the procedure, the mathematical model for measuring data depending on two variables, representing certain measuring values, can be based on the following equation:

$$MW_{a,b} = kn \cdot \sum_{i=1}^{p} NB_{a,i} \cdot NV_{i,b} + kf \cdot \sum_{j=1}^{q} FB_{a,j} \cdot FV_{j,b} + R_{a,b}$$

wherein $Mw_{a,b}$ is an measuring value, $NB_{a,i}$ is a contribution of useful information, $NV_{i,b}$ is an effect vector corresponding to an useful information, $FB_{a,j}$ is an error contribution, $FV_{j,b}$ is an effect vector corresponding to systematic measuring errors, $R_{a,b}$ is a residue, a and b are variables on which the measuring value depends, p is a number of carriers of useful information, q is a number of abstract error terms, and the scalars kn and kf are scaling factors for the contributions of useful information and the error contributions.

It is understood that in this and in all other equations of this protective right, the variables a and b may be interchanged.

In a chromatographic analyzing system designed as an absorption measuring system, in which the measuring data is generated in the form of absorption values according to the wavelength (spectra) and the time (chromatogram), it is particularly advantageous if the mathematical model is based on the following equation:

$$MW_{t,\lambda} = d \cdot \sum_{i=1}^{p} c_{t,i} \cdot \varepsilon_{i,\lambda} + \sum_{j=1}^{q} k_{t,j} \cdot Spec_{j,\lambda} + R_{t,\lambda}$$

wherein $MW_{t,\lambda}$ is an absorption value varying over time t and wavelength $\lambda$, d is a layer length of a flux cell, $c_{t,i}$ is a concentration of a substance i varying over time, i.e. a contribution of useful information of an effect vector characterizing an useful information, in this case the extinction coefficient, $\varepsilon_{i,\lambda}$, $k_{t,j}$ is an error contribution varying over time of an effect vector $Spec_{j,\lambda}$ corresponding to a systematic measuring error, $R_{t,\lambda}$ is a residue, p is a number of substances contributing to the absorption spectrum, and q corresponds to a number of abstract error terms.

In the case that, apart from the abstract effect vectors determined according to step $a_2$), which correspond to the systematic measuring errors, we know all effect vectors of the carriers of useful information corresponding to the useful information, i.e. the effect vectors of the useful information terms, in particular all spectra of the substances, the concentration course over time of a substance can be easily determined from the time course of the contributions of useful information and/or a substance amount, also representing an useful information can be determined with known calibration procedures.

If at least one spectrum of a substance to be analyzed is unknown, i.e. in the case that not all effect vectors of the terms of useful information are known, the missing spectrum or the missing effect vector of the substance of interest must be determined first. Four alternative procedures are particularly suitable to do this.

When doing so, it is practical to first determine the error contributions of the abstract effect vectors that correspond each to a systematic measuring error and were determined according to step $a_2$) for the measuring data obtained according to step $b_1$) for the variable a or b, for example the time, wherein those values of the variable or those points in time are measured for which the residue exceeds a certain limit due to an effect of certain carriers of useful information, for example an absorption peak, and reaches the limit again after an interval of values or after a time interval, and wherein subsequently the error contributions of the abstract effect vectors that correspond to systematic measuring errors are linearly interpolated for these values of the variables or for these points of time for the interval of values or the time interval in between so that the useful information which is corrected for systematical measuring errors in this interval of values or this time interval may be determined.

According to a first alternative, the estimated values of the true useful information, corrected for systematic measuring errors, can be determined with the linearly interpolated error contributions $FB'_{a,j}$ by using the following equation:

$$SW_{a,b} = MW_{a,b} - \sum_{j=1}^{q} FB'_{a,j} \cdot FV_{j,b}$$

wherein $SW_{a,b}$ is an estimated value of the useful information, $MW_{a,b}$ is an measuring value, $FB'_{a,j}$ are the error contributions linearly interpolated over time, $FV_{j,b}$ is an effect vector corresponding to systematic measuring errors, a and b are variables on which the measuring value depends, and q represents a number of abstract error terms. This procedure distinguishes itself by its simplicity.

For a chromatographic analyzing system designed as an absorption measuring system that is generating measuring data in the form of absorption values according to the wavelength and the time, it is practical if the estimated values of the true absorption values, corrected for systematic measuring errors by using linearly interpolated error contributions $k'_{t,j}$, are determined using the following equation:

$$A_{t,\lambda} = MW_{t,\lambda} - \sum_{j=1}^{q} k'_{t,j} \cdot Spec_{j,\lambda}$$

wherein $A_{t,\lambda}$ is an estimated value of the absorption, $MW_{t,\lambda}$ is an measuring value, $k'_{t,j}$ are the error contributions linearly interpolated over time, $Spec_{j,\lambda}$ is an effect vector corresponding to systematic measuring errors, t and $\lambda$ are the variables wavelength and time on which the measured absorption values depend, and q corresponds to a number of abstract error terms, that are superimposed over the measuring values.

According to a second alternative, it is practical if the error contributions of the abstract effect vectors are detennined for the measuring data detennined for the variable a or b according to step $b_1$) and the effect vectors each correspond to a systematic measuring error and were determined according to step $a_2$), wherein first those values of the variable are measured for which, due to an effect of certain carriers of useful information, the residue exceeds a certain limit and reaches this limit again after an interval of values, and wherein those error contributions are determined in a limited interval that correspond to either of the variables, a or b, and for which no useful information exists within the interval of values, and wherein the estimated values of the useful information, which were corrected for systematic measuring errors using these error contributions, are determined in the interval of values by using the equation $$SW_{a,b} = MW_{a,b} - \sum_{j=1}^{q} FB'_{a,j} \cdot FV_{j,b}$$

in the complete interval of the variable a or b.

For a chromatographic analyzing system designed as an absorption measuring system that generates measuring data in the form of absorption values according to the wavelength and the time, it is also practical to determine the error contributions of the abstract effect vectors for the measuring data, determined over time according to step $b_1$), that correspond each to a systematic measuring error and which were determined according to step $a_2$), wherein those points in time were determined first for which, due to the effect of a certain substance, i.e. for the occurrence of an absorption peak, the residue exceeds a certain limit and reaches the limit again after a time interval, and wherein those error contributions are determined in a limited wavelength interval in which the substance to be studied does not absorb, and wherein subsequently the estimated values of the absorption, which are corrected for systematic measuring errors by using these error contributions within the interval of time, are determined by applying the equation $$A_{t,\lambda} = MW_{t,\lambda} - \sum_{j=1}^{q} k'_{t,j} \cdot Spec_{j,\lambda}$$

over the entire wavelength interval.

In this procedure, the coefficients of the respective error effect vectors are therefore determined partially over a wavelength interval of which we know that the substance to be studied does not absorb. Consequently, the only previous information necessary is over which wavelength interval a certain substance or substance class absorbs, whilst the spectrum of this substance or substance class does not need to be known. The correction of the undesired effects is then performed with these partially determined coefficients.

According to a third alternative procedure, it is practical if an effect vector corresponding to the useful information of the carrier i of useful information causing the effect is determined by using the linearly interpolated error contributions FB' at a point $a_i$ wherein the residue reaches a maximum value and by applying the following equation:

$$NV_{i,b} = MW_{a_i,b} - \sum_{j=1}^{q} FB'_{a_i,j} \cdot FV_{j,b}$$

wherein $NV_{i,b}$ is the effect vector of the carrier i of useful information, $MW_{a_i,b}$ is the measuring value, $FB'_{a_i,j}$ are the linearly interpolated error contributions, $FV_{j,b}$ is the effect vector corresponding to the systematic measuring errors, and a and b are variables on which the measuring value depends, and wherein the thus determined effect vector corresponding to the useful information of the carrier of useful information is added to the abstract effect vectors corresponding to the systematic measuring errors, which was determined in step $a_2$) and wherein subsequently the effect vector contributions are determined for all effect vectors (useful information and errors) by using a mathematical procedure, in particular a linear regression. With these effect vector contributions, the useful information and the systematic error contributions can be determined. This alternative procedure assumes that at any given time, only one carrier of useful information contributes to the measured measuring value.

For a chromatographic analyzing system designed as an absorption measuring system that generates measuring data in the form of absorption values according to the wavelength and the time, it is particularly advantageous if a spectrum of the substance causing the effect (peak) is determined by using linearly interpolated error contributions $k'_{t_x,j}$ at a point of time $t_x$ wherein the residue reaches a maximum value and by applying the following equation:

$$\varepsilon_{x,\lambda} = MW_{t_x,\lambda} - \sum_{j=1}^{q} k'_{t_x,j} \cdot Spec_{j,\lambda}$$

wherein $\varepsilon_{x,\lambda}$ is the spectrum of the substance x causing the effect, $MW_{t_x,\lambda}$ is the absorption spectrum at the time $t_x$ over the wavelength $\lambda$, $k'_{t_x,j}$ are the error contributions determined of the j abstract effect vectors $Spec_{j,\lambda}$ over the wavelength $\lambda$ at the point of time $t_x$, and wherein the spectrum determined in this manner is added to the abstract effect vectors that correspond to the systematic measuring errors and which are determined according to step $a_2$), and subsequently their effect vector contributions k'' are determined for all effect vectors by using a mathematical procedure, more particularly a linear regression, and wherein these effect vector contributions can be used to determine the useful information and the error terms.

The coefficients k' of the effects at the position with the maximum, unexplained deviation are therefore determined with interpolation in this procedure. The unknown substance spectrum $\varepsilon_{x,\lambda}$ is then determined by correction of the effects, and this spectrum is included in the model of multi-linear regression. The regression calculation is then repeated over the peak. In this manner, the correct coefficient course $k''_{t,i}$ (relative concentration) of the unknown substance and of the error effect vectors can thus be calculated.

According to a fourth preferred alternative procedure, it is practical if all contributions of useful information and all systematic error contributions, contributing to the respective measuring values are determined in the interval of values or the time interval in which the residue exceeds a certain limit due to the superposition of sometimes more than one carriers of useful information and reaches the limit again after a certain interval of values or the time interval. To do so, the estimated values of the actual useful information, which are corrected for systematic measuring errors, are first determined using the linearly interpolated error contributions FB' or k'. Subsequently, the effect vectors contributing to the useful information of all carriers of useful information are calculated, using a mathematical procedure, such as a multi-component analysis. They are then added to the error effect vectors corresponding to the systematic measuring errors and the effect vector contributions $k''_{t,j}$, which can be used to determine the useful information and the systematic measuring errors, are then determined for all effect vectors, using a mathematical procedure, more particularly a multi-linear regression.

This procedure yields the most precise results and has the further advantage that even for not separated substances, the time course of concentrations for not completely separated peaks can be calculated by including additional spectra into the multi-linear regression model. In this case, it is effective to determine the spectra at least at the begin of the peak, at the peak maximum, and at the end of the peak. The spectra to be included in the multi-linear regression model are determined with known procedures, such as a multi-component analysis.

The actual useful information terms can then be determined from the effect vector contributions by applying the following equation:

$$SW_{a,b,i} = NB'_{a,i} \cdot NV_{i,b}$$

wherein $SW_{a,b,i}$ are true estimated values of the useful information of the carrier i of useful information, which depend on the variables a and b, $NB'_{a,i}$ are the effect vector contributions, and $Nv_{i,b}$ is the effect vector of the carrier i of useful information.

For a chromatographic analyzing system designed as an absorption measuring system that generates measuring data in the form of absorption values according to wavelength and time, it is particularly advantageous if the estimated values of the true absorption of the substance x causing the effect (peak) are determined by using the effect vector contributions k'', which were determined using multi-linear regression, and applying the following equation:

$$A_{t,\lambda,x} = k''_{t,x} \cdot \epsilon_{x,\lambda}$$

wherein $A_{t,\lambda,x}$ are the real estimated values of the useful information of the substance x, depending on the variables t and $\lambda$, $k''_{t,x}$ are the effect vector contributions, and $\epsilon_{x,\lambda}$ represent the spectrum of the substance x.

Using the estimated value of the actual useful information, for example the real absorption values, it is also advantageous to perform a plausibility check of the mathematical model used, by comparing the calculated estimated values with known values.

The invention also concerns a device for performing a procedure to process the measuring data that is measurable by using a measurement system, more particularly a chromatographic analyzing system, for the measurement of measuring values that correspond to certain useful information about, or of, a technical process and which depend on at least two variables, wherein a computation device for the determination of computed values from the measuring data and for their further processing is coupled with the measuring system, characterized by the following steps:

a) Performing a calibration step, including:

$a_1$) Stimulation of the measuring system by changing cause variables responsible for systematic measuring errors and determining the corresponding measuring data, using the measuring system;

$a_2$) Determination of effect vectors corresponding to systematic measuring errors from the measuring data obtained in step $a_1$) by using the computational device and a mathematical procedure, more particularly a factor analysis, wherein the effect vectors that correspond to the measuring errors are based on a mathematical model with which the measuring data can be estimated at least in approximation and wherein the model contains at least one error term containing an effect vector assigned to an measuring error and a corresponding error contribution;

b) Performing a measuring step, including:

$b_1$) Determining measuring data with the measurement system corresponding to certain useful information about, or of, the technical process while the technical process is taking place;

$b_2$) Reducing the measuring data gathered in step $b_1$) to linear components, based on the effect vectors determined in step $a_2$) that correspond to the measuring errors, by using the computational device and by applying a mathematical procedure, more particularly a linear regression procedure, in order to determine the error contributions with which useful information corrected for systematical measuring errors can be determined.

It is understood that the above-mentioned device is designed so that the procedure according to one or several of the embodiments described herein may also be, or is, performed advantageously in any possible combination.

BRIEF DESCRIPTION OF THE DRAWINGS

Other advantages, characteristics, and aspects of the invention can be seen from the following text that describes a preferred embodiment of the invention using the figures.

It is shown in.

DETAILED DESCRIPTION OF THE PREFERRED EMBODIMENT

The procedure according to the invention can be used advantageously to process measuring data that are determined by using a chromatographic analyzing system, wherein the measuring data corresponds to certain absorption values. These absorption values represent useful information about, or of, a technical process, wherein the process is a chromatographic substance analysis.

1. Measurement System

For the measurement system 10, an absorption measurement system 20 with a diode array sensor 26 is usually used for a chromatographic analysis. With the diode array sensor 26, the absorption values of the substances to be analyzed can be determined for certain measured wavelengths over time.

Figure 1:
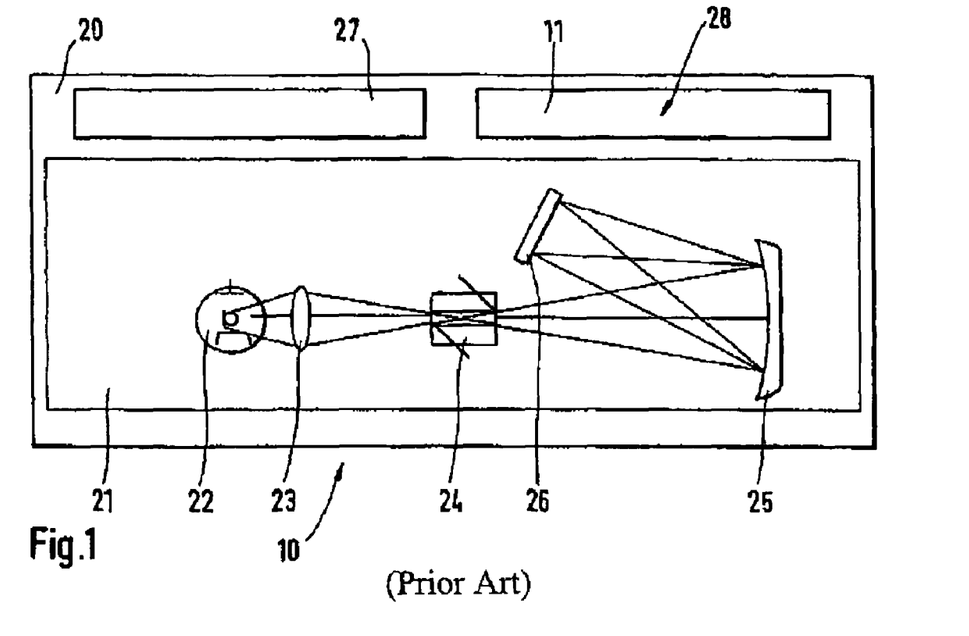
FIG. 1: a block diagram of a measurement system of the prior art, such as used in particular for an absorption measurement system for performing a chromatographic analysis.

The construction of such an absorption measurement system 20 can be seen from the block diagram shown in FIG. 1. The optical unit 21 of the absorption measurement system 20 contains the following essential elements: a light source 22, a lens or a lens system 23, a flux cell 24, a lattice 25, and a diode array sensor 26. The absorption measurement system 20 is supplied with electric energy by an energy source 27, and the measuring data is measured, stored, and analyzed using an electronic system 28. Accordingly, a computational device 11 and preferably also storage, representation, and/or analysis devices are coupled with the absorption measurement system 20.

For the light source 22, an electrical gas-discharge lamp is usually used. However, it is understood that other light sources, such as light emitting diodes, may also be used. The light source 22 radiates light of different wavelengths. The light is projected into a flux cell 24 with a beam generation device, in this case a lens 23, and through the flux cell 24 flows a fluid that may contain the substances or the substance mixtures to be analyzed. The light exiting from the flux cell hits a dispersive optical component, for example a lattice 25, that separates the light into it spectral parts and projects it onto the diode array sensor 26.

Since on one hand each individual photodiode of the diode array sensor 26 is only hit by light of one certain wavelength and on the other hand the necessary time of measurement to determine the measuring values is very short (a few milliseconds), the absorption values of the substance or substance mixture to be analyzed can be determined with respect to wavelength and time using the diode array sensor 26.

2. Structure of the Measuring Data

The measuring data determined with the absorption measurement system 20 in the form of absorption values of a chromatographic analysis depend on at least two variables, namely the wavelength (spectra) and the time (chromatograms). Consequently, a two-dimensional data structure is achieved that can be represented in form of a matrix as follows:

$$\begin{pmatrix} A_{t1,\lambda1} & A_{t1,\lambda2} & A_{t1,\lambda3} & \cdots & A_{t1,\lambda m} \\ A_{t2,\lambda1} & A_{t2,\lambda2} & A_{t2,\lambda3} & \cdots & A_{t2,\lambda m} \\ A_{t3,\lambda1} & A_{t3,\lambda2} & A_{t3,\lambda3} & \cdots & A_{t3,\lambda m} \\ \cdots & \cdots & \cdots & \cdots & \cdots \\ A_{tm,\lambda1} & A_{tm,\lambda2} & A_{tm,\lambda3} & \cdots & A_{tm,\lambda m} \end{pmatrix}$$

The spectra are arranged in rows or lines and the chromatographic signals are arranged in the columns of the matrix.

3. Model Creation

In the invention, it is assumed that this measuring data can be regarded as linear superposition of several individual pieces of information, namely useful information (the real absorption values), system-related error terms, and statistical uncertainties.

If from this data matrix, we firstly consider a spectrum at an arbitrary point in time $t_x$, the spectral course of these measuring values is a combination of the spectrum of the substance to be studied, the contributions of the system-related errors, and the noise. Instead of a substance, there may also be an impurity of the sample.

The useful information of a mixture of several substances is calculated by adding up the individual contributions of the respective substances. The same holds true for the systematic error terms. These contributions can also be considered as the sum of several independent individual contributions.

According to the Lambert-Beer law, a spectrum of a substance is defined as the product of the spectral characteristic (extinction $\epsilon_\lambda$), the effective length of the absorption (layer length of the flux cell d) and the concentration c of the substance.

$$A_{80} = d \cdot c \cdot \epsilon_\lambda$$

Or, for a mixture of substances:

$$A_\lambda = \sum_{i=1}^{p} A_{\lambda,i} = d \cdot \sum_{i=1}^{p} c_i \cdot \epsilon_{i,\lambda}$$

wherein $A_{\lambda,i}$ is the absorption spectrum of the substance number i, $\epsilon_{i,\lambda}$ is the extinction coefficient of the substance i, d is the layer length of the flux cell 24, $c_i$ is the concentration of the substance i, and p is the number of substances contributing to the absorption spectrum.

The contributions $ErrSys_\lambda$ of the error terms containing the systematic measuring errors can similarly be described as the sum of the products of the spectral characteristics $Spec_{j,\lambda}$ of the respective error term and a corresponding strength or a corresponding error contribution $k_j$:

$$ErrSys_\lambda = \sum_{j=1}^{q} k_j \cdot Spec_{j,\lambda}$$

wherein $\lambda$ is the wavelength and q is a number of abstract error terms.

At any point in time t, one measured spectrum can be described in general by the sum of the absorption contributions of the existing substances and the sum of the individual error contributions.

$$MW_\lambda = d \cdot \sum_{i=1}^{p} c_i \cdot \epsilon_{i,\lambda} + \sum_{j=1}^{q} k_j \cdot Spec_{j,\lambda} + R_\lambda$$

wherein $MW_\lambda$ is an absorption value varying over wavelength $\lambda$, d is a layer length of a flux cell, $c_i$ is a concentration of a substance i, i.e. a contribution of useful information of an effect vector characterizing an useful information, in this case the extinction coefficient $\epsilon_{i,\lambda}$, $k_j$ is an error contribution of an effect vector $Spec_{j,\lambda}$ corresponding to a systematic measuring error, $R_\lambda$ is a residue, p is a number of substances contributing to the absorption spectrum, and q corresponds to a number of abstract error terms.

Or, more generally:

$$MW_\lambda = \sum_{i=1}^{p+q} Coef_i \cdot Spectr_{i,\lambda} + R_\lambda$$

By including the time component, we obtain:

$$MW_{t,\lambda} = \sum_{i=1}^{p+q} Coef_{t,i} \cdot Spectr_{i,\lambda} + R_{t,\lambda}$$

The only time-dependent quantities here are the coefficient courses $Coef_{t,i}$ as a measure for the intensity of the individual contributions. With this consideration, the measuring data $MW_{t,\square\square}$ can be seen as linear components, consisting of the individual spectral characteristics $Spectr_{i,\lambda}$ representing a property of the useful information as well as the systematic errors, weighted with their respective strengths $Coef_{t,i}$.

In the case wherein the spectral characteristics of all terms are known, mathematical methods may be used to determine the coefficients $Coef_{t,i}$, and thus the individual contributions of the terms to the measuring result, at any point in time during the analysis.

According to the invention the spectral characteristics $Spec_{i,\lambda}$ of all imaginable system-related systematic error terms of the measurement system in a calibration cycle are determined. In the following analysis runs, those characteristics are used for the separation of the measured data into linear components. After the separation into linear components of the measured data, the undesired contributions due to systematic errors can be eliminated from the measuring data at any point in time or represented as individual contributions.

4. Stimulating the Measurement System

In order to be able to determine the spectral characteristics of the individual error terms, the measurement system is stimulated in a suitable manner during a calibration cycle. This means that influence quantities that cause systematic measuring errors are purposely changed, and the corresponding measuring data is determined with the measurement system 10 and effectively saved in a storage device (electronic system 28). Since consciously no useful information is created during the calibration cycle, the measuring data corresponds only to undesired effects (errors and solvent absorption). The terms "error effect vectors" or "effect vectors corresponding to systematic measuring errors" stand for the spectral characteristics of the error terms.

The requirements for the type and the course of the individual stimulation of the measurement system are derived from the existing system shortcomings and the expected measurement and environmental conditions. The main shortcomings of the system in the present case concern the region of the light source 22, the sensitivity of the measurement system 10 to fluctuations of the surrounding temperature, and the region of the flux cell 24 with occurring variations of the index of refraction, as well as solvent absorption.

Influence Quantity Surrounding Temperature

The fluctuations in the surrounding temperature, can be simulated for example by building a heating element into the cooling air stream. During the calibration cycle, certain changes of temperature are set and the reaction of the measurement system to these changes, i.e. the measuring data, are recorded to be analyzed later. Since the effect depends on the temperature propagation over time, the data are measured over a certain time interval. It is also possible to determine the temperature dependence by recording drift data during the heating phase of the measuring instrument.

However, the conditions in this case are only an approximation so that a limited accuracy of the results has to be expected. From the measuring data as a reaction to this stimulation the temperature-dependent effect vectors may be determined.

Influence Quantity Light Source

The stability of the plasma of a deuterium gas-discharge lamp is known to depend not only on the stability of the power supply but also on the variations of the plasma due to spatial expansion. Such spatial changes of the plasma are caused by physical processes during the gas discharge in the lamp. These properties of the light source result in several spectral error effect vectors, depending on the optical design of the irradiation system.

In order to determine these error effect vectors, the system can first be stimulated through simulation of the instability of the power supply by purposely varying the lamp current. For this purpose, the gas-discharge lamps are operated such that the plasma is stabilized by a constantly adjusted anode current after the ignition process of the plasma. The maintaining voltage resulting during the operation depends on a number of influential factors:

Distance between anode and cathode

Constitution of the cathode with respect to substance and form

Shape and homogeneity of the cathode material emitting the electrons

Deposits of materials on the wall of the lamp envelope

Temperature

Some of the above-mentioned influential factors depend on the construction or the design of the gas-discharge lamp. However, there are some influential factors that only affect the lamp over time. These influential factors are in particular fatigue effects of the cathode material. This can cause the maintaining voltage to change continuously, or sometimes erratically, so that the power consumption of the lamp, and thus also the radiation intensity may alter. A change of temperature also causes a change in the light intensity. The spectral characteristics of a change in intensity of the lamp by a change in power consumption is stimulated by purposely varying the lamp current.

Another stimulation is the simulation of the spatial movement of the plasma in the gas-discharge lamp. Do to so, the optic axis or the ray trajectory is transposed spatially in a suitable manner, and the reaction of the measurement system is determined. Defined shifts of the light ray in x, y, and z direction can be realized using a swaying plate in the optical ray trajectory. It is effective to insert a plane-parallel plate into the optical ray trajectory to deflect the optical axle by a parallel ray shift. The position of this plate can be changed in two rotational planes. In this manner, parallel ray shifts can be realized with the desired deflection in x and in y direction.

Influence Quantities Index of Refraction and Solvent Absorption

The spectral characteristics caused by physical processes in the flux cell 24 are due to absorption of the solvent, static and dynamic variation of the index of refraction because of created flow profiles, or striation. This suggests that the error effect vectors can be determined by stimulating these influence quantities.

The index of refraction is a property specific to the solvent or the substance and describes the optical density of the medium. The index of refraction has a merely static effect on the optical properties of the measurement system on one hand. On the other hand, there are dynamic processes in a flux cell causing local variations of the index of refraction due to differences of the concentration and of the solvent. Pressure and temperature disturbances have a similar effect on the optical properties. These causal influence quantities must be present in the creation of the stimulation so that the corresponding effect vectors may be generated. This can be achieved by variation of the solvent composition and by changes of the flow rate over the range required by the application.

At this point, however, it must become evident that an independent stimulation of the mentioned influence quantities is all but impossible. This is because in practical applications, the change of one quantity influences other quantities as well. Individual contributions can therefore only be determined in connection with other individual contributions.

If we assume that the contributions of the individual influence quantities are superimposed independently in their effects, the effect vector can still be determined with suitable mathematical methods.

5. Procedure for Determining the Error Effect Vectors

One suitable mathematical method for the extraction of the effect vectors is the procedure of factor analysis known from the multi-variant data analysis. The main application of factor analytical techniques is the reduction of the variables (effect vectors) and the revelation of structures in the relation between the variables. The procedure of factor analysis should be considered part of the subject of eigenvalue problems. As far as the factor analysis is concerned, there are a number of different algorithms and designations, which are denominated differently depending on the origin and the field of application.

This includes:

Principal component analysis

Principal axis analysis

Principal component analysis or principal component regression

Singular value decomposition, etc.

Such procedures can be applied using the computational device 10 to determine the corresponding abstract effect vectors from the measuring data gathered in the calibration cycle by stimulating the measurement system with the respective influence parameters.

A goal of the proposed procedure is to reduce the number of descriptive error effect vectors from the large amount of data from the calibration cycle by using factor-analytical methods and to develop a model that can be used to describe the properties of the system with the accuracy required in form of a limited number of abstract error effect vectors $Spec_{j,\lambda}$ and their receptive weights or error contributions $k_j$.

A procedure that has proven to be particularly suitable for this purpose is the singular value decomposition (SVD) procedure. The singular value decomposition method gives as a result a combined matrix consisting of three matrices.

wherein M is an original data matrix of measuring data, as a system response to the stimulation during the calibration cycle, U are the corresponding coefficient courses (scores), V are abstract spectral effect vectors (loadings), and $\Lambda$ is a diagonal matrix containing the square roots of the eigenvalues of $M^T*M$.

The factor loadings represent the connection in the ensemble of the measured calibration data in an abstract form. In the singular value decomposition (SVD) procedure, the factor loadings are determined sequentially according to their contributions to the variance of the data. If n spectra exist from the calibration run due to the created stimulation, the SVD procedure also yields n abstract spectral effect vectors. However, since it can be assumed that fewer influence quantities (error terms) describe the system behavior, far fewer factor loadings (effect vectors) are sufficient to describe the behavior of the system. The measuring data can be reconstructed for arbitrary time course and with sufficient accuracy by using a model made up of a reduced number of abstract effect vectors.

The number of abstract error effect vectors that must be selected to reconstruct the measuring data with the required accuracy can be derived from the singular values. Their value is measure of the contribution the respective effect vector makes to the variance of the data.

This can be illustrated with an example. It is assumed that the operating temperature of the measurement system causes two effects on the optical system; two thermal extensions, one in x direction, the other in y direction, each causing different spectral deviations. If we change only the temperature in one calibration run and we record the system response over time as a number of n spectra and we subject these spectra to a singular value decomposition, the result will be n abstract spectral vectors, but only two of these vectors significantly contribute to the variance of the data. This can be seen from the determined singular values that can be compared to the eigenvalues of the eigenvectors. From the values of the singular values of the abstract effect vectors, it can then be derived that the first two representatives have high values while the other effect vectors contribute to the variance only as noise.

This also offers the possibility of largely eliminating the statistical noise by excluding the spectral vectors that do not contribute significantly to the variance of the measuring data from the model creation.

The model creation of the systematic influence quantities is the better, the larger the spectral vectors are, i.e. the higher the number of data points per spectrum and the more spectra are available from the calibration cycle.

6. Measuring Step

As described above, the invention proposes to first stimulate the measurement system 10 with suitable influence quantities. From the recorded data, abstract effect vectors are determined by using mathematical methods and the computational device 11. Using these effect vectors, the characteristics of the undesired shortcomings of the individual system can be described.

After this calibration step or cycle, analytical measurements are subsequently performed. For this purpose, the individual substances of the sample (substance mixtures) to be studied, which were separated using chromatographic separation methods, are analyzed individually. At any point in time, the measuring data (spectra) are separated into linear components using mathematical methods with the help of the computational device 11 based on the abstract effect vectors used. This means that the coefficients or error contributions, i.e. the strength of the respective effects are continuously determined, preferably by using multi-linear regression, while the chromatographic analysis is performed, consequently while the absorption data is recorded over wavelength and time.

In the case that there is no unknown substance at a given point in time, the measured spectra can be explained entirely by the coefficients of the effect vectors, i.e. by the error contributions and the coefficients of known effect vectors for useful information. These again are a result of the multi-linear regression analysis.

If however an unknown spectrum, for example the spectrum of one of the substances to be measured, is contained in the measured spectrum, the result of the multi-linear regression will be an unexplained deviation, i.e. a residue that exceeds a certain limit. This indicates the existence of a disregarded spectral characteristic or the absorption of a substance.

After the chromatographic peak subsides, a state is reached again wherein the data can be explained completely. Since the contributions of the effects, i.e. the effect vectors weighted with the corresponding coefficients, are now determined before and after the peak, the contributions of the error effect vectors can now be eliminated from the measuring data during the peak. This can be done in one of several ways.

For this purpose, the error contributions of the abstract effect vectors can be determined for the measuring data determined according to step $b_1$) over the time with the help of the computational device 11. The effect vectors, each corresponding to a systematic measuring error, were determined according to step $a_2$), wherein those points in time were measured where, due to an effect of certain carriers of useful information, in this case therefore the absorption of a substance or a substance mixture to be studied, the residue exceeds a certain limit and reaches this limit again after a time interval. The error contributions of the abstract error effect vectors are then linearly interpolated at these points in time so that the useful information that has been corrected for the systematic measuring errors, in this case therefore the real absorption values, may be determined in this time interval. Consequently, the coefficients of the corresponding effect vectors in the peak interval are linearly interpolated first.

Then the measuring data or the spectra can be corrected for the individual contributions of the undesired effects. The result is the estimated real absorption contribution of the substance to be studied. A number of alternative procedures may be applied to correct the measuring data.

According to the first alternative procedure already described, the estimated values of the absorption values over wavelength and time, which were corrected for systematic measuring errors, can be derived from the linearly interpolated error contributions $k'_j$ by applying the following equation:

$$A_{t,\lambda} = MW_{t,\lambda} - \sum_{j=1}^{q} k'_{t,j} \cdot Spec_{j,\lambda}$$

wherein $A_{t,\lambda}$ is an estimated value of the absorption, $MW_{t,\lambda}$ is an measuring value, $k'_{t,j}$ are the error contributions linearly interpolated over time, $Spec_{j,\lambda}$ is an effect vector corresponding to systematic measuring errors, t and $\lambda$ are the variables wavelength and time on which the measured absorption values depend, and q corresponds to a number of abstract error terms.

According to the second alternative procedure, the error contributions of the abstract effect vectors can be determined for the measuring data gathered over time according to step $b_1$) by using the computational device 11. The effect vectors each correspond to a systematic measuring error and were determined according to step $a_2$), wherein those points of time were measured where, due to an effect of certain substance, the residue exceeds a certain limit and reaches this limit again after a time interval, and wherein those error contributions are determined in a limited wavelength interval in which the substance to be studied does not absorb. The estimated values of the absorption in the time interval, corrected for systematic measuring errors with the help of the error contributions, are then determined in the complete wavelength interval by applying the previous equation.

This means that in this alternative procedure, the coefficients of the corresponding abstract error effect vectors are determined partially over a wavelength interval about which it is known that the substance to be studied does not absorb. The correction of the undesired effects is then performed with these partially determined coefficients.

The most precise results and other important advantages can be achieved by applying the third or fourth alternative procedure. In these procedures, the unknown substance spectrum or spectra are first determined. Then these spectra are included in the model of the multi-linear regression, and the regression calculation is repeated over the peak or the peak cluster with the aid of the computational device 11. This yields the correct coefficient course, i.e. also the relative concentrations of the unknown substances. The substance amount can be calculated by using known calibration procedures.

The spectrum of the substance causing the effect, i.e. the absorption peak, can be determined with the aid of the linearly interpolated error contributions at a time wherein the residue reaches a maximum value, by applying the following equation:

$$\varepsilon_{x,\lambda} = MW_{t_x,\lambda} - \sum_{j=1}^{q} k'_{t_x,j} \cdot Spec_{j,\lambda}$$

wherein $\varepsilon_{x,\lambda}$ is the spectrum of the substance x causing the effect, $MW_{t_x,\lambda}$ is the measured absorption spectrum at the point of time $t_x$ over the wavelength $\lambda$, $k'_{t_x,j}$ are the error contributions of the j abstract effect vectors $\text{Spec}_{j,\lambda}$ determined over the wavelength $\lambda$ at the point of time $t_x$, and wherein the spectrum determined in this manner is added to the effect vectors corresponding to the systematic measuring errors determined in step $a_2$). Subsequently, the effect vector contributions k" are determined for all effect vectors by using a mathematical procedure, more particularly a linear regression. With the effect vector contributions the real absorption values, which are estimated values, and the systematic error terms can be determined.

It is also possible to determine the spectrum $\epsilon_{x,\lambda}$ creating the absorption peak by a weighted determination of average over selected time intervals over the peak using the linearly interpolated error contributions.

The estimated values of the real absorption of the substance causing the effect (peak x) are effectively determined by using the effect vector contributions and applying the following equation:

$$A_{t,\lambda,x} = k''_{t,x} \cdot \epsilon_{x,\lambda}$$

wherein $A_{t,\lambda,x}$ are the real estimated values for the absorption of the substance x, depending on the variables t and $\lambda$, $k''_{t,x}$ are the effect vector contributions as a measure for the relative concentration, and $\epsilon_{x,\lambda}$ is the spectrum of the substance x.

The estimated values of the error terms superimposed over the measuring value can be effectively determined by using the error effect vector contributions and applying the following equation:

$$\text{ErrSys}_{t,\lambda,y} = k''_{t,y} \cdot \text{Spec}_{y,\lambda}$$

wherein $\text{ErrSys}_{t,\lambda,y}$ are the real estimated values of the error terms y, depending on the variables t and $\lambda$, $k''_{t,y}$ are the effect vector contributions as a measure for the error contributions, and $\text{Spec}_{x,\lambda}$ is the error characteristic of the error term y.

Figure 2:
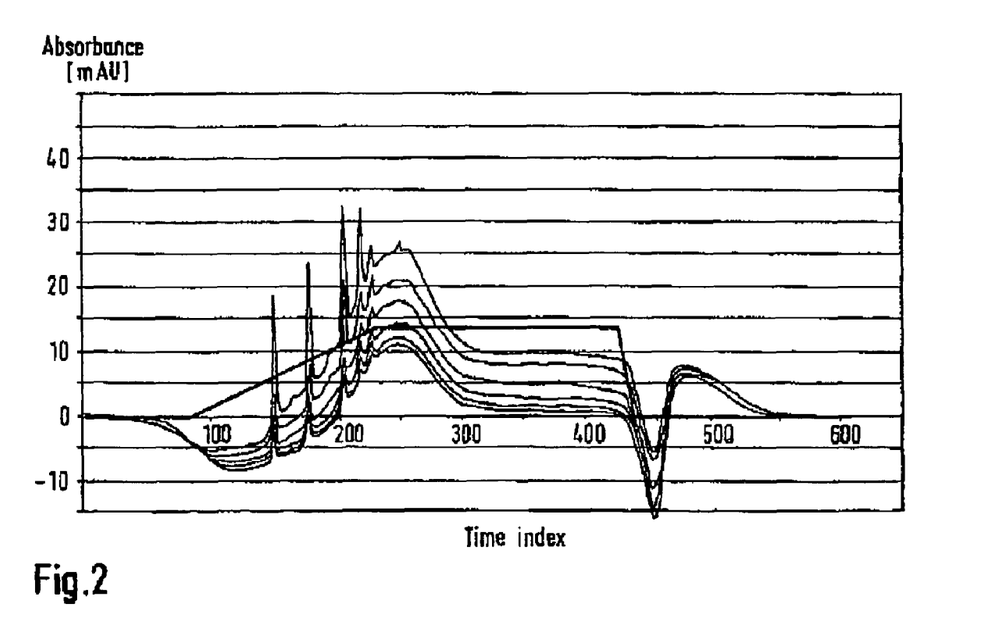
FIG. 2: a graphical representation of measuring data gained in a chromatographic analysis, that shows the absorption data for different wavelengths and over time as well as a corresponding course of a solvent composition of a solvent gradient.

In the following, the results before and after the application of the procedure for processing measuring data according to the invention are illustrated as an example with two diagrams:

FIG. 2 shows a graphical representation of the absorption course over time for different wavelengths as measured in a chromatographic analysis. The curves correspond to the chromatographic signals measured for several wavelengths, which were recorded simultaneously. The superposition of useful information and the effects of systematic error terms can be seen clearly. The stretched course of the measurement signal with undershoots and overshoots is caused by the systematic error terms, due to index of refraction and flux effects. These courses are then superimposed by effects due to absorption of the solvent and by the peaks of the substances to be studied. The time course of the selected solvent composition can be seen from the bold full line with linear sections.

Figure 3:
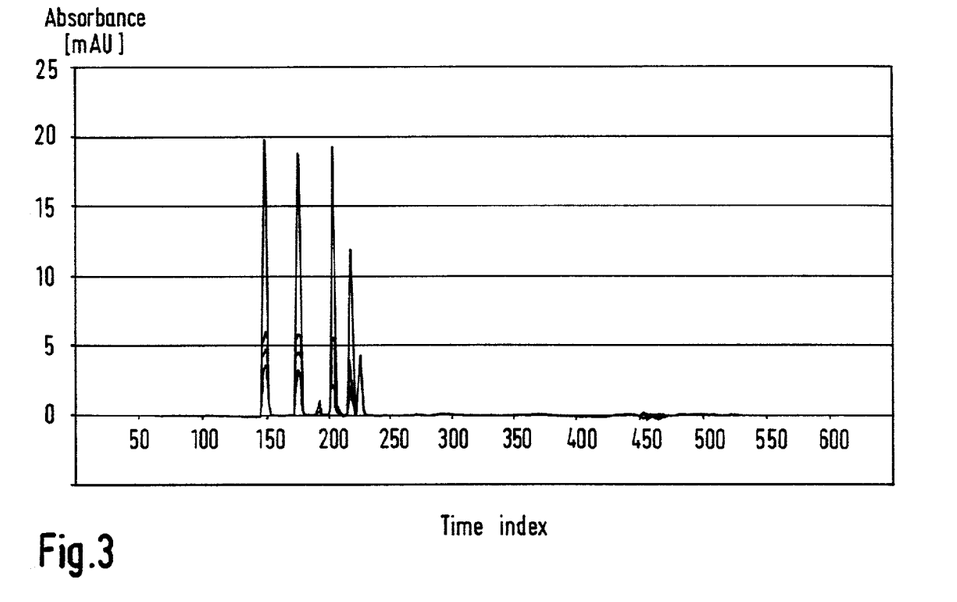
FIG. 3: a graphical representation of estimated values of the absorption values for different wavelengths over time, as determined according to the invention.

FIG. 3, on the other hand, illustrates the result after performing the proposed procedure for the extraction of useful information in the form of the correct absorption courses over time for different wavelengths of the respective substances. It is evident that the quantitative analysis of the measurement signals can be made more precisely.

In practice it is desirable to provide results online rather than using the calculation device 11 to perform the calculations offline at the end of an analysis. This can be achieved by dynamically changing the mathematical model during the analysis.

When doing so, only those effect vectors are included in the mathematical model firstly that were determined in a previous calibration cycle. As long as no peak or peak clusters exist, or after it has worn off, the variance of the measured spectrum can be explained at any point in time by the error effect vectors and their measured coefficients or the error contributions. When a peak occurs, the model is extended by temporarily including the participating spectrum of the unknown substance in the model. The calculation over the peak/peak cluster is then repeated with the modified model. Then the spectra are removed from the model again and the calculation is continued until the next peak/peak cluster is detected, and the procedure continues in this manner. The computational treatment of the data over a peak or a peak cluster can be refined arbitrarily by using this or other procedures.

An advantage of the dynamic model creation is that the calculations performed with the aid of the computational device 11 can be performed virtually in real time during an analysis and the complexity of the calculation does not increase with the number of substances in an analysis.

The result of this procedure is a matrix of the coefficients in which the time course of the concentrations of the substances to be studied and the coefficient courses of the effect vector are contained.

$$k_{t,v} = \begin{pmatrix} k_{t0,v0} & k_{t0,v1} & k_{t0,v2} & \cdots & k_{t0,vm} \\ k_{t1,v0} & k_{t1,v1} & k_{t1,v2} & \cdots & k_{t1,vm} \\ k_{t2,v0} & k_{t2,v1} & k_{t2,v2} & \cdots & k_{t2,vm} \\ \cdots & \cdots & \cdots & \cdots & \cdots \\ k_{tn,v0} & k_{tn,v1} & k_{tn,v2} & \cdots & k_{tn,vm} \end{pmatrix} \begin{matrix} \text{Vectors(substances, errors)} \\ \\ \text{Time} \end{matrix}$$

wherein n is the number of vectors (substances errors) considered in the mathematical model, and m is the number of data points of a measurement over time.

The columns of the matrix of the coefficients represent the time course of the respective substance or effect. In the given case the first three columns are meant to correspond to the courses of the dissolved concentrations of up to three possible substances in a peak cluster, while the other columns of the matrix of the coefficients are reserved for the courses of the modeled effects.

It should be observed that the time course of the concentration is pieced together according to the peak detection. This must be considered in the reconstruction of the data or the determination of the substance amounts. Since the respective concentration courses already correspond to the relative concentrations of the wanted substances, the determination of the substance amounts is particularly easy.

The absorption of a substance x to be studied depending on the time and wavelength results from the vector multiplication:

$$A_{t,\lambda,x} = k''_{t,x} \cdot \epsilon_{x,\lambda}$$

When using the alternative procedures 1 and 2, the real absorption of an unknown substance is determined from the measured data by eliminating the contributions of all error terms. However, this has the disadvantage that most of the noise superimposed over the measuring data remains or may even become worse.

The contributions of all terms considered in the mathematical model can be easily determined or combined arbitrarily and can be interpreted for diagnostic purposes.

The linear component decomposition of the measuring data is the better, the longer the spectral vectors, i.e. the larger the number of data points per spectrum. For the remaining noise, this means that its contribution to the coefficient course decreases with increasing number of data points per spectrum. For a vector length of 256 data points, the remaining noise is reduced by more than one order of magnitude. This advantage is neither at the expense of the time resolution nor at the expense of the spectral resolution as it is the case for filter procedures used in the past.

Consequently, the application of the proposed procedure opens another possibility for increasing the accuracy in the determination of the results by reducing the remaining noise in the signals. Furthermore, the limit of detectability in a chromatographic analysis may be lowered. Consequently, it becomes possible to detect and analyze reliably smaller effects than in the past.

Figure 4:
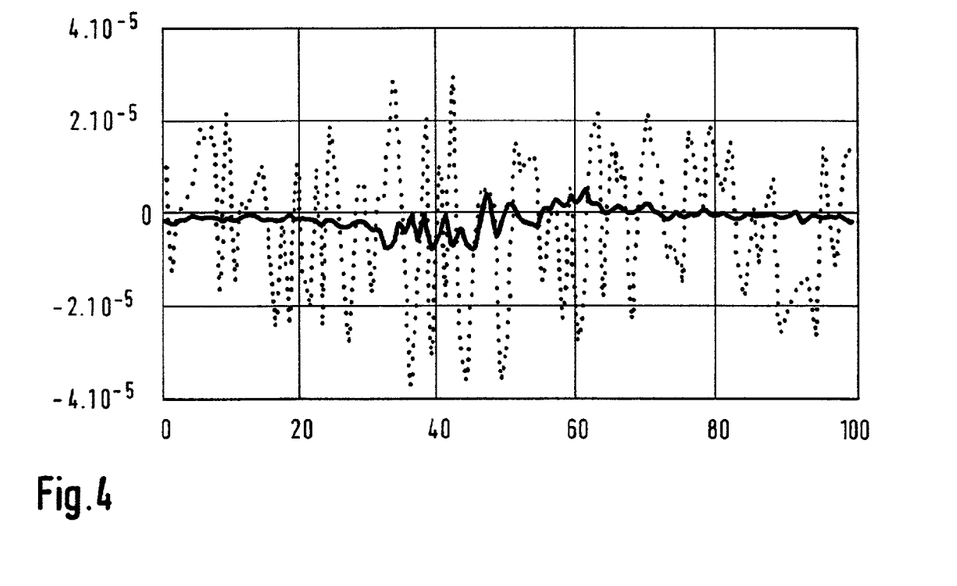
FIG. 4: a graphical representation of noise contributions before and after the application of the procedure according to the invention.

FIG. 4 shows a time course of the measurement signal before and after performing the procedure according to the invention. The dotted line refers to the course of the measurement signal before applying the procedure according to the invention. The course of the measurement signal shown with a full line represents the result after applying the procedure according to the invention. If we compare the standard deviation as a measure for the noise, then we observe an improvement by a factor of more than six for a chosen vector length of more than 50 data points. As previously mentioned, the reduction of the noise contribution is not achieved by filtering the data. With an increasing number of data points of the spectral vectors, we achieve increased statistical reliability in the model creation, resulting in a reduction of the remaining noise. The time and spectral resolution remain unaffected by this.

A basic thought behind the invention is that measuring data may be represented by a superposition of useful information, systematic error terms and static noise. By separation of the measuring data into linear components with suitable mathematical procedures, using the computational device 11, the error contributions of the systematic error terms, the contributions of useful information of the useful information terms, and the contributions of the static noise may be determined with the aid of the computational device 11.

The procedure can be applied to measurement systems 10 that generate data in at least two dimensions. The procedure consists of a calibration step and a measuring step. The calibration step consists of a complete determination of the system-related behavior characteristics by suitable stimulation and extraction of the effect vectors from the calibration data with the aid of the computational device 11. In the measuring step, measuring data of, or about, useful information of interest is separated into linear components while a technical processes is taking place by applying a dynamically changing mathematical model with the aid of the computational device 11. The separation starts with the system-related error effect vectors and includes or removes vectors of useful information when useful information or effects due to carriers of useful information occur or subside. In case of a measurement system 10 designed as a chromatographic analyzing system, the vectors of useful information correspond to the spectral vectors, and the useful information corresponding to the carriers of useful information are the absorption peaks correlated with the substances to be analyzed or the sample-related impurities.

With this procedure it is also possible to apply computational methods to separate peaks that are not completely separated. Even entire peak clusters can be analyzed correctly.

The result of the procedure is the correct coefficient courses of all components contributing to the measuring result. For the substances to be studied, this corresponds to the relative concentration course, which in this case is not derived from an individual chromatographic signal but corresponds to the strength of an entire spectrum. For the error terms, this corresponds to the respective error contributions of the error effect vectors. Since a large number of data points contribute to the determination of the result in this procedure, the statistical security is increased. The remaining noise is therefore reduced significantly.

Essential Contributions of the Invention:
Improvement of the accuracy and precision of the measuring results by largely eliminating superimposed error terms or system-related and sample-related disturbances.
Improvement of the limit of detectability by canceling the remaining noise.
Correct determination of the concentration courses of not completely separated substances.
High plausibility of the results by separation of the measuring data into linear components and consequent assignment and detection of the respective individual contributions.
High plausibility of the measuring results by automatic detection of unexplained parts in the measuring data.
Reduction in cost by reducing the requirements for the components of the measurement system or the detector by the possibility to eliminate error contribution by computation.

The invention claimed is:

1. A method for processing measuring data from a measuring system, wherein the method comprises:
a) calibrating the measuring system, wherein said calibrating includes:
$a_1$) stimulating the measuring system by changing cause variables responsible for systematic measuring errors of the measuring system, and determining corresponding measuring data; and
$a_2$) determining effect vectors corresponding to systematic measuring errors from the measuring data obtained in step $a_1$) by using a mathematical method, wherein the effect vectors are based on a mathematical model with which the measuring data is estimated, wherein the mathematical model contains an error term containing an effect vector assigned to a measuring error and a corresponding error contribution;
b) measuring, using the measuring system, wherein said measuring includes:
$b_1$) obtaining measuring data that corresponds to information concerning a process, while the process is taking place, and that depends on at least two variables; and
$b_2$) transforming the measuring data gathered in step $b_1$) to linear components, based on the effect vectors determined in step $a_2$),
$b_3$) using a mathematical method that corrects said transformed measuring data from step $b_2$) for said systematic measuring errors; and
$b_4$) outputting the corrected transformed measuring data from step $b_3$.

2. A method according to claim 1, wherein said information is determined from the measuring of data by application of mathematical algorithms on which the mathematical model is based, by taking into account the error contributions.

3. A method according to claim 1,
wherein the mathematical model, for measuring of data dependent on two variables representing certain measuring values, is based on the following equation:

$$MW_{a,b} = kn \cdot \sum_{i=1}^{p} NB_{a,i} \cdot NV_{i,b} + kf \cdot \sum_{j=1}^{q} FB_{a,j} \cdot FV_{j,b} + R_{a,b}$$

wherein $Mw_{a,b}$ is an measuring value, $NB_{a,i}$ is a contribution of said information, $NV_{i,b}$ is an effect vector corresponding to an information, $FB_{a,j}$ is an error contribution, $FV_{j,b}$ is an effect vector corresponding to systematic measuring errors, $R_{a,b}$ is a residue, a and b are variables on which the measuring value depends, p is a number of carriers of information, q is a number of abstract error terms, and the scalars kn and kf are scaling factors for the contributions of information and the error contributions.

4. A method according to claim 3,
wherein the error contributions of the abstract effect vectors that correspond each to a systematic measuring error and which were determined according to step $a_2$), are determined for the measuring data obtained according to step $b_1$) over the variable a or b, for example the time,
wherein those values of the variable or those points in time are measured for which the residue exceeds a certain limit due to an effect of certain carriers of information and reaches the limit again after an interval of values or after a time interval, and
wherein subsequently the error contributions of the abstract effect vectors that correspond to systematic measuring errors are linearly interpolated for these values of the variables or for these points of time for the interval of values or the time interval in between so that the information which are corrected for systematical measuring errors in this interval of values or this time interval may be determined.

5. A method according to claim 4,
wherein estimated values of the information corrected for the systematic measuring errors by using the linearly interpolated error contributions, are determined according to the following equation:

$$SW_{a,b} = MW_{a,b} - \sum_{j=1}^{q} FB'_{a,j} \cdot FV_{j,b}$$

wherein SW is an estimated value of the information, MW is an measuring value, FB' are error contributions linearly interpolated over the values of the variables or the time, FV is an effect vector that corresponds to systematic measuring errors, a and b are variables on which the measuring value depends, and q represents a number of abstract error terms.

6. A method according to claim 4,
wherein for a chromatographic analyzing system designed as an absorption measuring system which generates measuring data in the form of absorption values according to the wavelength and the time, estimated values of the absorption values which are corrected for systematical measuring errors are determined by using linearly interpolated error contributions, by using the following equation:

$$A_{t,\lambda} = MW_{t,\lambda} - \sum_{j=1}^{q} k'_{t,j} \cdot Spec_{j,\lambda}$$

wherein A is an estimated value of the absorption, MW is an measuring value, k' are error contributions interpolated linearly over time, Spec is an effect vector corresponding to systematic measuring errors, t and λ represent the variables time and wavelength, respectively, on which the measured absorption values depend, and q is a number of abstract error terms.

7. A method according to claim 4,
wherein an effect vector corresponding to the information of the carrier of information causing the effect is determined by using the linearly interpolated error contributions at a point where the residue reaches a maximum value and by applying the following equation:

$$NV_{i,b} = MW_{a_i,b} - \sum_{j=1}^{q} FB'_{a_i,j} \cdot FV_{j,b}$$

wherein $NV_{i,b}$ is an effect vector of the carrier i of information, $MV_{ai,b}$ is an measuring value, $FB'_{aj,j}$ are linearly interpolated error contributions, $FV_{j,b}$ is an effect vector corresponding to the systematic measuring errors, and a and b are variables, on which the measuring value depends, and
wherein the effect vector corresponding to the information of the carrier of information determined in this manner is added to the abstract effect vectors corresponding to the systematic measuring errors and determined according to step $a_2$), and
wherein subsequently the effect vector contributions of these effect vectors are determined with which the information can be determined by using a mathematical method.

8. A method according to claim 7,
wherein estimated values of the information, which have been corrected for systematic measuring errors, are determined by using effect vector contributions and by applying the following equation:

$$SW_{a,b,i} = NB''_{a,i} \cdot NV_{i,b}$$

wherein $SW_{a,b,i}$ are real estimated values of the information of the carrier i depending on the variables a and b, $NB''_{a,i}$ are effect vector contributions, and $NV_{i,b}$ is an effect vector of the carrier i of information.

9. A method according to claim 4,
wherein, in the interval of values or in the time interval in which the residue exceeds a certain limit and reaches the limit again after an interval of values or a time interval caused by the superposition of several carriers of information, all contributions of information and all systematic error contributions contributing to the corresponding measuring values are determined, and wherein the estimated values of the real information, which have been corrected for systematic measuring errors by using the linearly interpolated error contributions, are first determined and then the effect vectors that correspond to the information of all carriers of information are calculated by using a mathematical method and wherein theses effect vectors are subsequently added to the error effect vectors corresponding to the systematic measuring errors, and wherein for all effect vectors, their effect vector contributions are subsequently determined using a mathematical method and wherein the effect vector contributions can be used to determine the information and the systematic measuring errors.

10. A method according to claim 4, wherein for a chromatographic analyzing system designed as an absorption measuring system which generates measuring data in the form of absorption values according to the wavelength and the time, a spectrum of the substance causing the effect is determined by using linearly interpolated error contributions at a point of time where the residue reaches a maximum value and by applying the following equation:

$$\varepsilon_{x,\lambda} = MW_{t_x,\lambda} - \sum_{j=1}^{q} k'_{t_x,j} \cdot Spec_{j,\lambda}$$

wherein $\varepsilon_{x,\lambda}$ is a spectrum of the substance x causing the effect, $MW_{t_x,\lambda}$ is a measured absorption spectrum at a time $t_x$ over the wavelength $\lambda$, $k'_{t_x,j}$ are error contributions of j abstract effect vectors $Spec_{j,\lambda}$ over the wavelength $\lambda$ at the time $t_x$, and wherein the spectrum determined in this manner is added to the abstract effect vectors that correspond to the systematic measuring errors and which are determined according to step $a_2$), and subsequently their effect vector contributions are determined for all effect vectors by using a mathematical method and wherein these effect vector contributions can be used to determine the information corrected for systematic measuring errors.

11. A method according to claim 10, wherein the estimated values of the absorption of the substance causing the effect (peak) are determined by using the effect vector contributions and by applying the following equation:

$$A_{t,\lambda,x} = K''_{t,x} \cdot \varepsilon_{x,\lambda}$$

wherein $A_{t,\lambda,x}$ are real estimated values of the information of the substance x, depending on the variables t and $\lambda$, $k''_{a,i}$ are effect vector contributions, and is a spectrum of the substance x.

12. A method according to claim 3, wherein the error contributions of the abstract effect vectors that correspond each to a systematic measuring error and which were determined according to step a2), are determined for the measuring data obtained according to step $b_1$) for the variable a or b, wherein those values of the variables are determined for which the residue exceeds a certain limit due to an effect of certain carriers of information and reaches the limit again after an interval of values, and wherein those error contributions are determined in a limited interval corresponding to one of the variables a or b, for which there is no information within the interval of values, and wherein these error contributions are used to determine estimated values which are corrected for systematic measuring errors within the interval of values by using the following equation:

$$SW_{a,b} = MW_{a,b} - \sum_{j=1}^{q} FB'_{a,j} \cdot FV_{j,b}$$

wherein SW is an estimated value of the information, MW is an measuring value, FB' are error contributions linearly interpolated over the values of the variables or the time, FV is an effect vector that corresponds to systematic measuring errors, a and b are variables on which the measuring value depends, and q represents a number of abstract error terms, for the complete interval of the variable a or b.

13. A method according to claim 3, wherein for a chromatographic analyzing system designed as an absorption measuring system which generates measuring data in the form of absorption values according to the wavelength and the time, the error contributions of the abstract effect vectors that correspond each to a systematic measuring error and which were determined according to step $a_2$) are determined for the measuring data determined according to step $b_1$) over the time, wherein those points in time were determined for which, due to an effect to a certain substance, the residue exceeds a certain limit and reaches the limit again after a time interval, and wherein those error contributions are determined in a limited wavelength interval in which the substance to be studied does not absorb, and wherein subsequently estimated values of the absorption, which are corrected for systematic measuring errors are determined by using these error contributions within the interval of time by applying the following equation:

$$A_{t,\lambda} = MW_{t,\lambda} - \sum_{j=1}^{q} k'_{t,j} \cdot Spec_{j,\lambda}$$

wherein A is an estimated value of the absorption, MW is an measuring value, k' are error contributions interpolated linearly over time, Spec is an effect vector corresponding to systematic measuring errors, t and μ represent the variables time and wavelength respectively, on which the measured absorption values depend, and q is a number of abstract error terms, in the entire wavelength interval.

14. A method according to claim 1, wherein the mathematical model which generates measuring data in the form of absorption values according to the wavelength and the time, is based on the following equation:

$$MW_{t,\lambda} = d \cdot \sum_{i=1}^{p} c_{t,i} \cdot \varepsilon_{i,\lambda} + \sum_{j=1}^{q} k_{t,j} \cdot Spec_{j,\lambda} + R_{t,\lambda}$$

wherein MW is an absorption value varying with the time t and the wavelength $\lambda$, d is the layer length of a flux cell, c is the concentration of a substance i, i.e., a contribution of information of an effect vector characterizing information, in this case an extinction coefficient $\varepsilon$, k is an error contribution of the effect vector (Spec) corresponding to a systematic measuring error, R is a residue, p is a number of substances contributing to the absorption spectrum, and q represents a number of abstract error terms.

15. The method according to claim 1, wherein said outputting comprises storing said corrected transformed measuring data from step $b_4$.

16. The method according to claim 1, further comprising deriving further data from said corrected transformed measuring data from step $b_4$.

17. A device for processing measuring data from a measuring system, wherein said device, when coupled with the measuring system, performs a method comprising:
   a) calibrating the measuring system, wherein said calibrating includes:
      $a_1$) stimulating the measuring system by changing cause variables responsible for systematic measuring errors of the measuring system, and determining corresponding measuring data; and
      $a_2$) determining effect vectors corresponding to systematic measuring errors from the measuring data obtained in step a1) by using a mathematical method, wherein the effect vectors are based on a mathematical model with which the measuring data is estimated, wherein the mathematical model contains an error term containing an effect vector assigned to a measuring error and a corresponding error contribution;
   b) measuring, using the measuring system, wherein said measuring includes:
      $b_1$) obtaining measuring data that corresponds to information concerning a process while the process is taking place, and that depends on at least two variables; and
      $b_2$) transforming the measuring data gathered in step $b_1$) to linear components, based on the effect vectors determined in step $a_2$),
      $b_3$) by using a mathematical method that corrects said transformed measuring data from step $b_2$) for said systematic measuring errors; and
      $b_4$) outputting the corrected transformed measuring data from step $b_3$.

18. The device according to claim 17, wherein said outputting comprises storing said corrected transformed measuring data from step $b_4$.

19. The device according to claim 17, wherein said device further performs an activity of deriving further data from said corrected transformed measuring data from step $b_4$.

* * * * *